(12) United States Patent
Kristiansson et al.

(10) Patent No.: US 6,355,216 B1
(45) Date of Patent: Mar. 12, 2002

(54) METHOD OF STERILIZING CLOSED CONTAINERS

(75) Inventors: Anders Kristiansson, Lund; Jan Andersson, Stad, both of (SE)

(73) Assignee: Tetra Laval Holdings & Finance SA, Pully (CH)

( * ) Notice: Subject to any disclaimer, the term of this patent is extended or adjusted under 35 U.S.C. 154(b) by 0 days.

(21) Appl. No.: 09/284,044

(22) PCT Filed: Sep. 19, 1997

(86) PCT No.: PCT/SE97/01576

§ 371 Date: Jan. 3, 2000

§ 102(e) Date: Jan. 3, 2000

(87) PCT Pub. No.: WO98/16287

PCT Pub. Date: Apr. 23, 1998

(30) Foreign Application Priority Data

Oct. 14, 1996 (SE) ................................................ 9603736

(51) Int. Cl.$^7$ .................................................. A61L 9/15
(52) U.S. Cl. ............................ 422/29; 422/22; 422/28
(58) Field of Search .............................. 422/22, 28, 29

(56) References Cited

U.S. PATENT DOCUMENTS

| | | | | | |
|---|---|---|---|---|---|
| 5,250,257 | A | * | 10/1993 | Lengfelder | 422/22 |
| 5,855,856 | A | * | 1/1999 | Karlson | 422/22 |
| 6,085,492 | A | * | 7/2000 | Moller et al. | 53/426 |

* cited by examiner

*Primary Examiner*—Robert J. Warden, Sr.
*Assistant Examiner*—Sean E. Conley
(74) *Attorney, Agent, or Firm*—James Ray & Associates

(57) ABSTRACT

In a method of sterilizing containers the container is first sealed and then subjected to electron irradiation. The ozone generated in this way is then retained in the closed container for the purpose of sterilizing the same.

7 Claims, 1 Drawing Sheet

Figure 1:
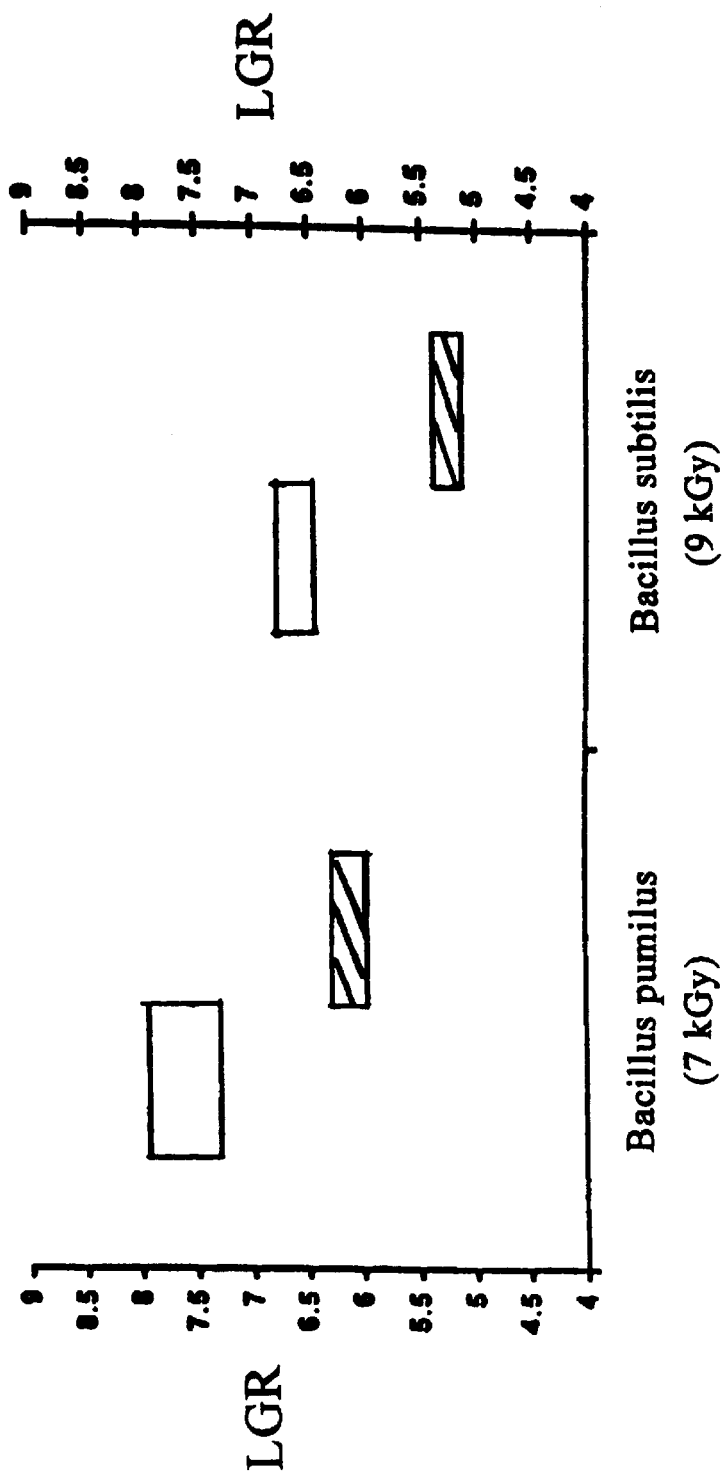

Bacillus pumilus (7 kGy)     Bacillus subtilis (9 kGy)

METHOD OF STERILIZING CLOSED CONTAINERS

The present invention refers to a method of sterilizing a container.

Within the food industry there is a great need to be able to sterilize containers which are manufactured as closed containers and which when subsequently filled can be opened, filled, and sealed under sterile conditions. Furthermore, there is a great interest from the market for an aseptic bottle of polyethylene terephtalate (PET). The aseptic treatment of a package material such as polyester is rather unusual since this type of material is mostly used for soft drinks and the like.

Electron guns have been used for food containers for the purpose of sterilizing relatively thin containers from the outside, and for several years the sterilization method has been contemplated for further use within the packaging industry. When a commercial plastic bottle is irradiated from one side with a relatively low energetic and thus cheap commercial electron generator it is relatively simple to sterilize the cubic content within the bottle as well as smooth surfaces on the inside of the container. However, when other places in the bottle, such as its neck and bottom part, are concerned the material at those places is so thick and the radiation due to the low energy is so low that a sufficient lethal effect cannot be achieved. Different systems have thus been developed in order to obtain an effective sterilization within this type of container, the sterilization being achieved via the open part of the container.

The sterilizing effect of electrons has been known for a long time. Electron irradiation is a generally known sterilization method, and the mechanism behind the lethal effect has been thoroughly studied. The main lethal mechanism of the irradiation is that these electrons within a cell break bonds in the DNA chain.

One problem with electron beam sterilization has constantly been that ozone always is formed during the irradiation of the material to be sterilized. When sterilizing by this method, which mainly is performed on non-closed containers in close connection with the filling of the container, great efforts have been spent on taking care of this poisonous gas. This can be achieved by passing the container through a heater with sterile air, the ozone formed being inactivated and/or ventilated away to the greatest possible extent. Alternatively, surplus ozone can be removed with nitrogen or the sterilizing process can be performed in vacuum. However, all these procedures are costly.

A further problem is that the ozone formed in turn can react with the package material, and the reaction products obtained can give an off flavor when solubilized from the material. Thus, the ozone generated is considered to result in product limitations in that sensitive products are more difficult to pack.

The purpose of the invention is to provide a method of the kind mentioned by way of introduction, which method allows a more effective sterilization of closed containers in a cheap and simple way, the problems mentioned above being eliminated.

In order to achieve this purpose the method according to the invention has been given the characterizing features of claim 1.

In order to further explain the invention reference is made to the accompanying drawing, in which FIG. 1 shows the killing of microorganisms as a logarithmic reduction (LGR) after electron irradiation of sealed PET bottles containing air (empty rectangles) or helium (hatched rectangles).

During an electron irradiation in air the oxygen therein is converted to ozone. However, the different effects caused by ozone is not as well studied as those which have been caused by electron irradiation. Ozone is known to be a strong oxidant of organic substances, but the prospects of using ozone has been limited by the high investment and operating costs for its production. However, it is considered that the ozone molecules—in the form of activated oxygen—by means of chain reaction give rise to what is called free radicals which result in that biomolecules (DNA, RNA, enzymic and structural proteins, and saturated fatty acids, etc.) are changed and destroyed. Thus, several, maybe all enzymes in a cell can be influenced by the oxidative change of their catalytic or allosteric centra.

The air which has been activated by means of electron irradiation is according to the invention utilized in that the container is sealed before the electron irradiation is started and the ozone formed is retained within the closed container for the purpose of sterilizing the same. Thus, an environment rich in ozone is produced, which during a suitable and necessary period of time is allowed to exert its effect so that a satisfactory sterilization is obtained.

However, it has been found that the ozone formed has half-lives which are very dependent on its environment, i.e. the material in the vicinity of the $O_3$-molecules. The half-life depends on such parameters as the humidity of the air as well as the temperature and it can vary from about ten seconds to several days. A too rapid degradation in a closed container would result in that the required sterilizing dosage [f(time, concentration)] becomes too low.

Experiments were thus performed with PET bottles for the purpose of ascertaining whether the ozone formed in a closed container together with the ozone generating electron irradiation would be able to produce an effective sterilization by permitting the ozone to have a certain period of time to act.

EXAMPLE 1

Determination of the half-life for ozone.

In order to determine the degradation of the ozone generated by irradiating closed PET containers a 300 keV electron beam and an analyzer Ozomat MP Ozone (Anseros, Germany) were used. The ozone was generated with an acceleration voltage of 300 keV and a dosage of 20 kGy in sixty PET bottles which had been subjected to a small pressure above the atmospheric for the purpose of avoiding the penetration of air. The ozone concentrations in the bottles were then followed for 12.5 h.

With this electron irradiation treatment a half-life of about 5 h was determined. The half-life was estimated to be sufficiently long for obtaining a sterilizing effect in microorganisms which already have been damaged by the exposure to electrons.

EXAMPLE 2

Examination of the presence of any off-flavor after ozone treatment.

In order to elucidate if off-taste problems are achieved in PET bottles of 350 ml, in which ozone has been induced by means of electron irradiation, and in order to examine whether exposure to ozone for a long period of time has such an effect a series of experiments was performed by using an electron gun with an energy level of 300 keV. In this connection the bottles obtained strong overdoses, i.e. twice as much as the dosage required for sterilization. The dosages were determined by means of a Far West Radiachromic reading device (Far West Technologies, Calif., USA).

Bottles containing ozone generated in air were compared with bottles irradiated with electrons in an inert atmosphere. Thus, sealed PET bottles of 350 ml were tested by means of four different treatments:

1. The bottles contained air and were irradiated with an average dosage of 25 kGy;
2. The bottles contained air and were irradiated with an average dosage of 40 kGy;
3. The bottles contained nitrogen gas and were irradiated with an average dosage of 25 kGy;
4. The bottles contained air and were not irradiated but treated as a reference example.

After the irradiation the bottles were allowed to stand for about 24 hours, and they were then opened and filled with filtered water. After a further incubation of nine days at room temperature a sensory analysis was performed in order to quantify the off-flavor, which in a taste testing panel was graded from 0 (no off-flavor) to 3 (strong off-flavor).

All the bottles treated were considered to have an acceptable small off-flavor. Thus, no significant differences could be attributed to a difference in dosage level or to different atmospheres in the bottles.

EXAMPLE 3

Examination of the lethal effect after ozone treatment.

In this series of experiments the effect of ozone in electron irradiated PET bottles was examined with reference to the number of killed microorganisms. *Bacillus pumilus* ATCC 27242 and *Bacillus subtilis* NCA 7252 were used as test organisms. The capacity of killing these organisms was determined as the logarithmic reduction which was defined as the number of organisms in a reference sample minus the number of surviving organisms.

PET bottles were inoculated with one of the test organisms and exposed to an electron gun (10 MeV, Risö National Laboratories) with doses of 7 and 9 kGy, respectively, the bottles then being filled with 50 ml culture broth for each organism. The bottles were incubated and afterwards analyzed to assess whether any growth occurred in the bottles or not. The results in comparison with reference samples were statistically evaluated in a customary way (based on the method with "Most Probable Number") which is well known to the man skilled in the art.

FIG. 1 shows the logarithmic reduction of *B. pumilus* and *B. subtilis* in helium and air (30% relative humidity) with radiation dosages of 7 and 9 kGy, respectively, for the two microorganisms.

When irradiating PET bottles containing a reactive or a non-reactive atmosphere, i.e. air or helium, respectively, a significant difference in logarithmic reduction was obtained after electron irradiation. Thus, the logarithmic reduction was 25% higher for *Bacillus subtilis* and 20% higher for *Bacillus pumilus* when the irradiation was performed in air in comparison with an atmosphere of helium. In this connection it could be established that the ozone generated in the containers drastically effected the reduction in the number of microorganisms.

By the simultaneous as well sequential utilization according to the invention of the two sterilizing methods electron irradiation and ozone treatment not only an additive effect but also a synergistic effect is obtained, which is surprising. Furthermore, other experiments suggest that also a supplementary effect is achieved in that radiation resistant organisms are not at the same time resistant to ozone and vice versa.

Without in any way being bound to a specific theory or mechanism of action the effects obtained by the sterilization according to the invention could be due to the following. When sterilizing with for example 25 kJ per kg this corresponds to about $10^9$ electrons being passed through a microorganism during the sterilization process, and only a small part of these electrons will result in a directly lethal effect in the form of destruction of DNA. However, all the electrons pass through the cell membrane and will then generate membrane damages which weaken the organism and result in an increased probability of the ozone generated by the electron irradiation more easily being able to penetrate into the cell. Once inside the cell the ozone can exert its additive effect. A supplementary effect can be explained by the two sterilization methods being able to act in different ways. The effect becomes synergistic in that the ozone destroys enzymes, and then above all in that the enzymatic DNA repair mechanisms are eliminated.

The ability of the electrons to penetrate a package material is relatively low but depends of course on the radiation energy. Thanks to the invention the energy level required for electron irradiation is not influenced by the container locally having a large material thickness, such as for example the neck of a bottle. In that way energy levels less than 300 keV can be utilized, which results in that commercially available equipment can be utilized.

An important advantage of the method according to invention is that the unfilled container used is manufactured closed and impervious. Thus, the generation as well as the degradation of the poisonous gas takes place inside an already pre-sealed container. When the container is subjected to electron irradiation a certain sterilization takes place and at the same time ozone is formed. Before the container is filled the ozone is allowed to act for such a long period of time that its action together with the initial effect of the electron irradiation results in a sufficient sterilization of the container. Since it takes much time to repair the injuries obtained from an electron irradiation it can be necessary to make use of a long storage time with ozone in the container.

While the sterilization process still proceeds after the treatment of the container by means of electron irradiation the container is transported to the place of filling, where the container is filled and resealed in a sterile environment. If the time between the sterilization and the filling of the container is sufficiently long the ozone concentration will decrease. Consequently, the inconvenience of handling a poisonous gas is reduced when the container is filled. It is thus possible to let the degradation proceed to such a length that the ozone content is harmless when the container is opened in the filling machine.

However, the ozone content can according to the invention also be adjusted by modifying the atmosphere within the container. For example, the amount of ozone generated in the container can be increased by the addition of more oxygen to the container before it is sealed. Furthermore, the degradation rate of the ozone can be decreased by lowering the temperature in the container. Correspondingly, an increased degradation rate is obtained when the temperature is increased. Any remaining residual ozone in a container can thus be eliminated by heating the container directly before the filling procedure.

The degradation rate can also be increased by raising the humidity in the container. By controlling the humidity in the container the water activity is also controlled, which in turn influences the death rate of the microorganisms during the sterilization process.

What is claimed is:

1. Method of sterilizing a container, characterized by the steps of sealing the container, subjecting the container to electron irradiation, ozone being generated within the container, and retaining the ozone generated in the closed container for the purpose of sterilizing the same.

2. Method as claimed in claim 1, characterized in that the container is stored after the electron irradiation but prior to its filling.

3. Method as claimed in claim 1, characterized in that energy levels lower than 300 keV are utilized for the electron irradiation.

4. Method as claimed in claim 1, characterized in that the amount of ozone within the container is adjusted by modifying its atmosphere.

5. Method as claimed in claim 4, characterized in that the atmosphere is modified by changing the amount of oxygen in the container.

6. Method as claimed in claim 4, characterized in that the atmosphere is modified by changing the humidity in the container.

7. Method as claimed in claim 4, characterized in that the atmosphere is modified by changing the temperature in the container.

* * * * *